(12) United States Patent
Cuesta Frau et al.

(10) Patent No.: US 8,315,698 B2
(45) Date of Patent: Nov. 20, 2012

(54) METHOD AND APPARATUS FOR AUTOMATIC ANALYSIS OF T-WAVE ALTERNANS

(75) Inventors: David Cuesta Frau, Alcoi (ES); Pedro Mateo Riobo Aboy, Beaverton, OR (US)

(73) Assignee: Universidad Politecnica de Valencia, Alcoi (ES)

( * ) Notice: Subject to any disclaimer, the term of this patent is extended or adjusted under 35 U.S.C. 154(b) by 553 days.

(21) Appl. No.: 12/480,349

(22) Filed: Jun. 8, 2009

(65) Prior Publication Data

US 2009/0306526 A1 Dec. 10, 2009

Related U.S. Application Data

(60) Provisional application No. 61/059,866, filed on Jun. 9, 2008.

(51) Int. Cl.
*A61B 5/0472* (2006.01)
(52) U.S. Cl. ......... 600/517; 600/515; 600/516; 600/518
(58) Field of Classification Search ................ 607/4–11, 607/17, 30; 600/481, 508–510, 513–518
See application file for complete search history.

(56) References Cited

U.S. PATENT DOCUMENTS

2003/0069512 A1* 4/2003 Kaiser et al. .................. 600/516
2009/0192394 A1* 7/2009 Guttag et al. .................. 600/509

OTHER PUBLICATIONS

Cuesta-Frau et al. Enhanced modified moving average analysis of T-wave alternans using a curve matching method: a simulation study. Med Biol Eng Computing. 2009. 47:323-331 (Published Online: Oct. 2008).
Narayan SM. T-Wave Alternans and the Susceptibility to Ventricular Arrhythmias. Journal of the American College of Cardiology. vol. 47, No. 2, 2006.

* cited by examiner

*Primary Examiner* — Rex R Holmes
(74) *Attorney, Agent, or Firm* — Mateo Aboy; Aboy & Associates PC (57) ABSTRACT

The invention disclosed includes a method and apparatus for calculation of T-wave alternas in electrocardiographic (ECG) signals; said method comprises the following method steps: (a) collecting and storing an ECG signal; (b) detecting each heartbeat T-wave in the ECG signal using an automatic detection and segmentation algorithm; (c) classifying said heartbeat T-wave as an even or odd heartbeat T-wave; (d) initializing said method by taking the first even and the first odd heartbeat T-wave as their respective initial average; (e) processing all the heartbeat T-waves in the ECG signal to generate an even heartbeat T-wave weighted average and odd heartbeat T-wave weighted average; and (f) calculating TWA using a distance metric between the even heartbeat weighted average and the odd heartbeat weighted average, said distance metric including curve matching Continuous Dynamic Time Warping (CDTW).

3 Claims, 8 Drawing Sheets

METHOD AND APPARATUS FOR AUTOMATIC ANALYSIS OF T-WAVE ALTERNANS

CROSS REFERENCE TO RELATED APPLICATIONS

This application claims the priority benefit of PPA No. 61/059,866 filed on Jun. 9, 2008 by the present inventors, which is incorporated by reference.

FEDERALLY SPONSORED RESEARCH

Not Applicable.

SEQUENCE LISTING OR PROGRAM

Not Applicable.

BACKGROUND

1. Field of Invention

This invention relates to methods and apparatus for calculation of T-wave alternans (TWA). Specifically, it relates to methods and apparatus for obtaining quantitative measurements of TWA from electrocardiogram (ECG) signals.

2. Prior Art

The introduction of digital electrocardiography and digital computing has enabled the clinical use of advanced signal processing techniques and the detection of subtle electrocardiogram features of clinical significance. Some of these features are not detectable by expert visual inspection but have proven to be important markers for serious heart illnesses [16]. An example of such a feature is T-wave alternans (TWA).

T-wave alternans (TWA) are beat-to-beat amplitude oscillations in the T-waves of electrocardiograms. Numerous clinical studies have demonstrated the link between these oscillations and ventricular arrhythmias.

Several methods have been developed in recent years to detect and quantify TWA, and use it as a non-invasive test to identify patients who are at increased cardiac risk. Timedomain analysis methods of TWA involve subtracting T-waves of even versus odd beats as in the commercially available MMA method [11].

Repolarization is the electrophysiological phenomenon associated with the recovery of cardiac cells after their excitation. T-waves in an ECG are the electrical manifestation of this repolarization process and may reflect electrical disturbances in normal electrophysiology associated with some cardiac diseases. Thus, T waves provide physicians with indicators of cardiac abnormalities and a means to assess therapy.

T-waves correspond to the ECG manifestation of the differences in action potential durations in the myocardium. The beginning of the T-wave is linked to the first cells that repolarize, and the end of the T-wave is defined by the last cells in repolarizing. The contour of the complete wave is directly related to the path of repolarization, and alterations have a counterpart in the shape of the T-wave. This phenomenon can occur on a beat to beat basis, as in TWA.

Ventricular repolarization heterogeneity has been demonstrated to constitute a risk indicator of possible malignant arrhythmias and sudden cardiac death [11]. In the past, measuring the duration of QT interval (or QT dispersion, QTd) was the only way to assess ventricular repolarization. However, the QT interval does not provide information about any abnormality of the repolarization sequence. Additionally, the QT interval is innaccurate due to measurement and QT interval normalization problems [6], and because of some technical drawbacks related to T-wave end detection [1].

In recent years, the research community has also developed methods to detect and quantify TWA. Some of the most widely employed methods in clinical practice are [8]:

Spectral methods. A time series is created by taking samples from consecutive T-waves, and then the Fourier spectrum is computed. Peaks at frequency 0.5 Hz indicate the presence of TWA [14].

Complex demodulation method. The same time series as in the previous case is demodulated and low pass filtered. Amplitude and phase of the alternans are derived from this filtered signal [12].

Correlation method. A single cross-correlation coefficient is computed for every ST-T complex against a representative for a heartbeat series. If the correlation index alternates for some consecutive beats, a TWA episode is detected [2].

Poincare mapping. Poincare maps are formed by plotting T-wave magnitude of alternate beats [16]. Semiperiodic signals such as TWA, appear as tight clusters. TWA magnitude is the intercluster distance.

MMA. TWA magnitude is obtained by means of the maximum absolute difference of even and odd heartbeat series averages computed at T waves or ST-T complexes [13].

SUMMARY

In its most basic form, the invention includes a method and apparatus for calculation of T-wave alternas in electrocardiographic (ECG) signals; said method comprises the following method steps: (a) collecting and storing an ECG signal; (b) detecting each heartbeat T-wave in the ECG signal using an automatic detection and segmentation algorithm; (c) classifying said heartbeat T-wave as an even or odd heartbeat T-wave; (d) initializing said method by taking the first even and the first odd heartbeat T-wave as their respective initial average; (e) processing all the heartbeat T-waves in the ECG signal to generate an even heartbeat T-wave weighted average and odd heartbeat T-wave weighted average; and (f) calculating TWA using a distance metric between the even heartbeat weighted average and the odd heartbeat weighted average, said distance metric including curve matching. According to one embodiment said distance metric is computed as maximum absolute value of the difference between the event heartbeat. According to a second embodiment of the present invention, a method of curve matching is used prior to calculating the distance metric. In a third embodiment, the distance metric includes a similarity metric based on Dynamic Time Warping (DTW). According to a forth embodiment, the distance metric is based on Continuous Dynamic Time Warping (CDTW). The method can be implemented in firmware or software as part of a microcontroller or microprocessor-based apparatus for calculation of TWA. According to one embodiment, said apparatus comprises: (a) sensors and data acquisition hardware to acquire and store said ECG signal; (b) means for processing said ECG signals using said method implemented in firmware or software in order to automatically calculate TWA; and (c) means for displaying said TWA such as a flat-panel display, a computer display, a PDA display, or a smartphone display.

DETAILED DESCRIPTION

This invention relates to methods and apparatus for calculation of TWA. Specifically, it relates to methods and apparatus for obtaining quantitative measurements of TWA from electrocardiogram (ECG) signals.

Figure 1:
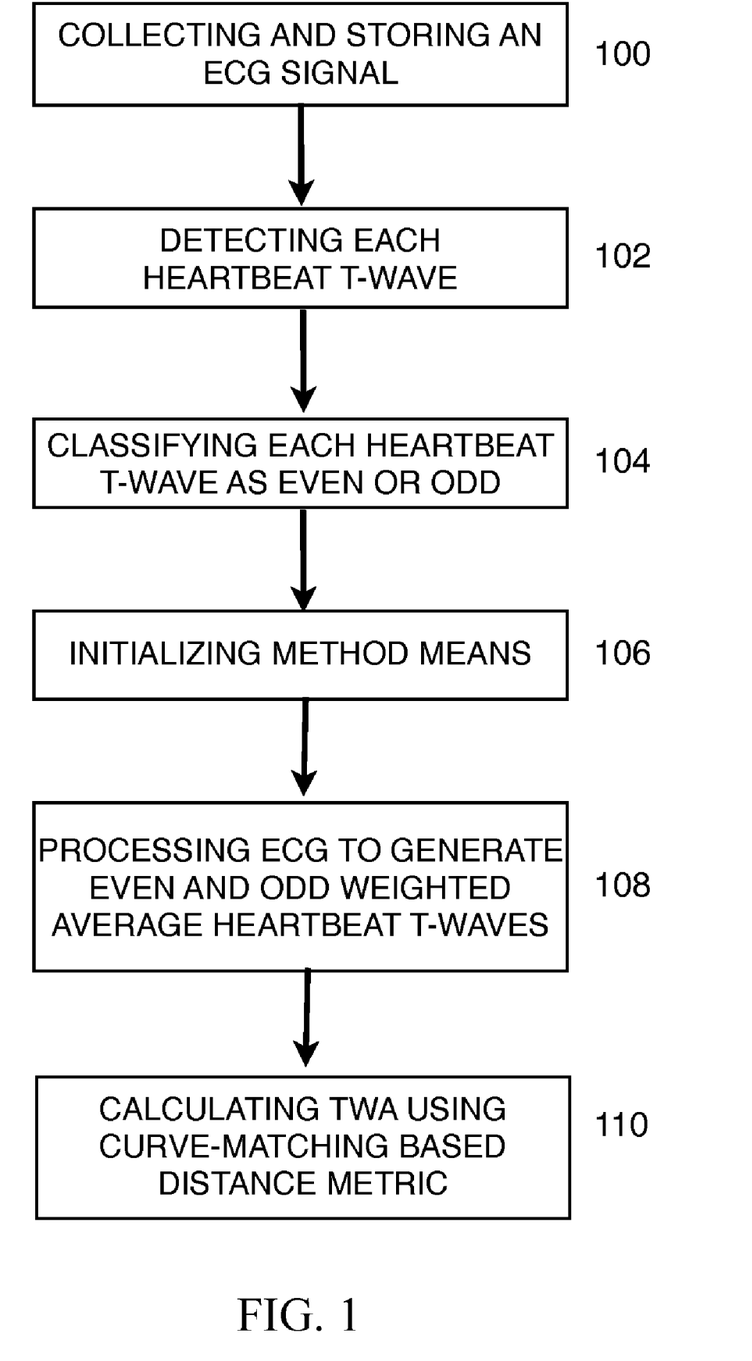
FIG. 1 shows a block diagram of an embodiment of the present invention illustrating the method steps required to compute TWA using a curve matching-based distance measure.
Figure 2:
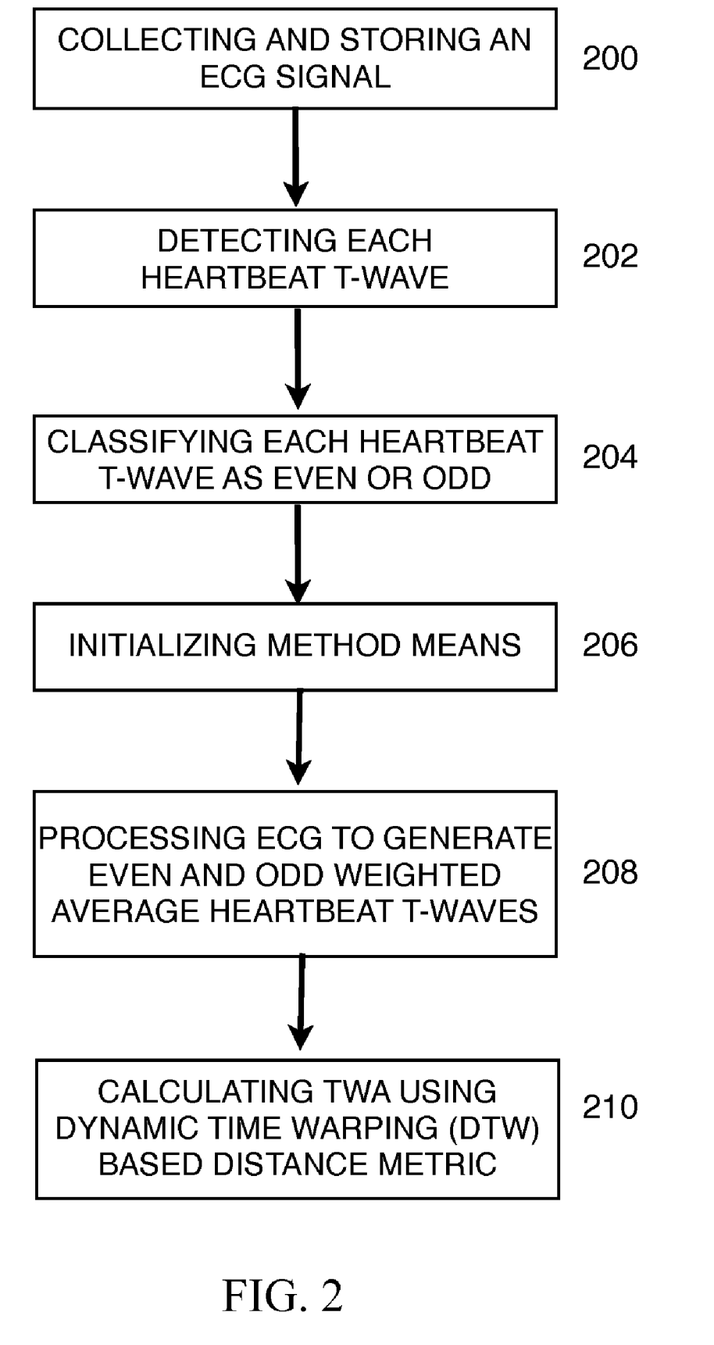
FIG. 2 shows a block diagram of an embodiment of the present invention illustrating the method steps required to compute TWA using Dynamic Time Warping.
Figure 3:
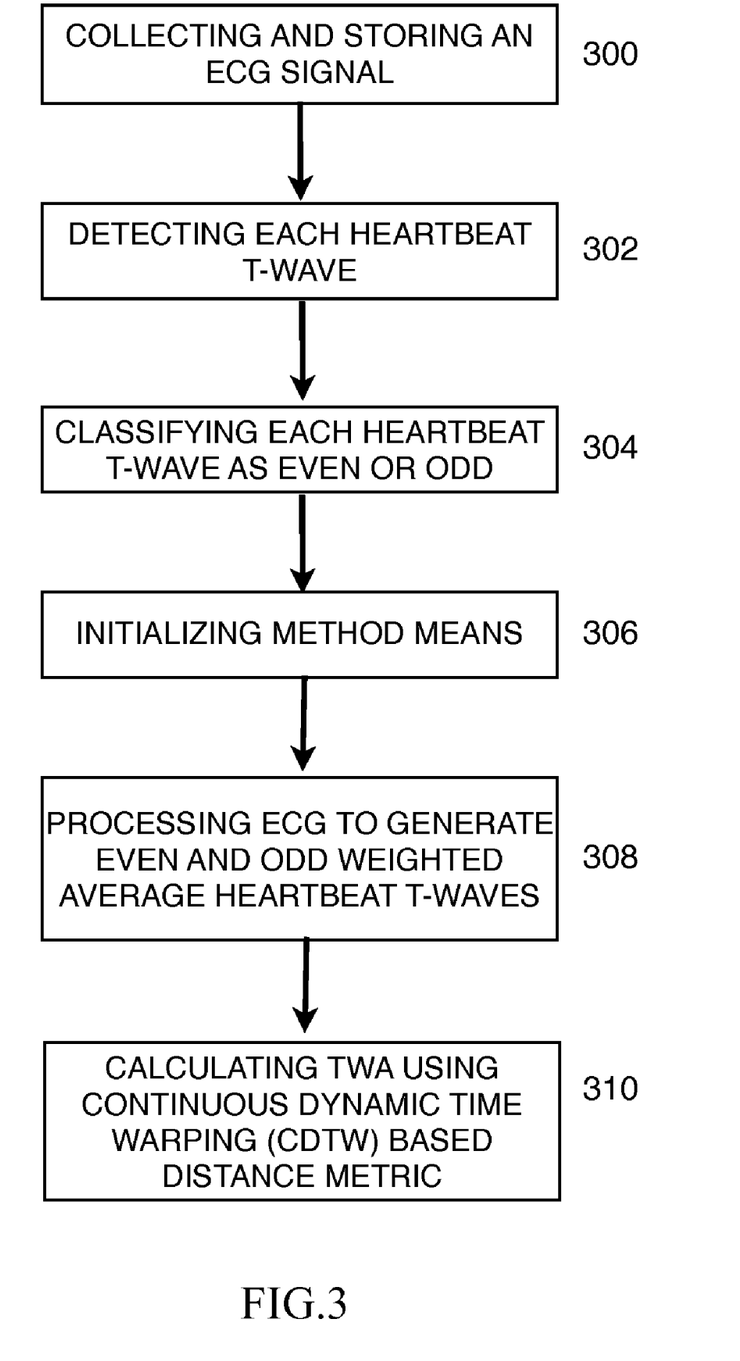
FIG. 3 shows a block diagram of an embodiment of the present invention illustrating the method steps required to compute TWA using Continuous Dynamic Time Warping.
Figure 6:
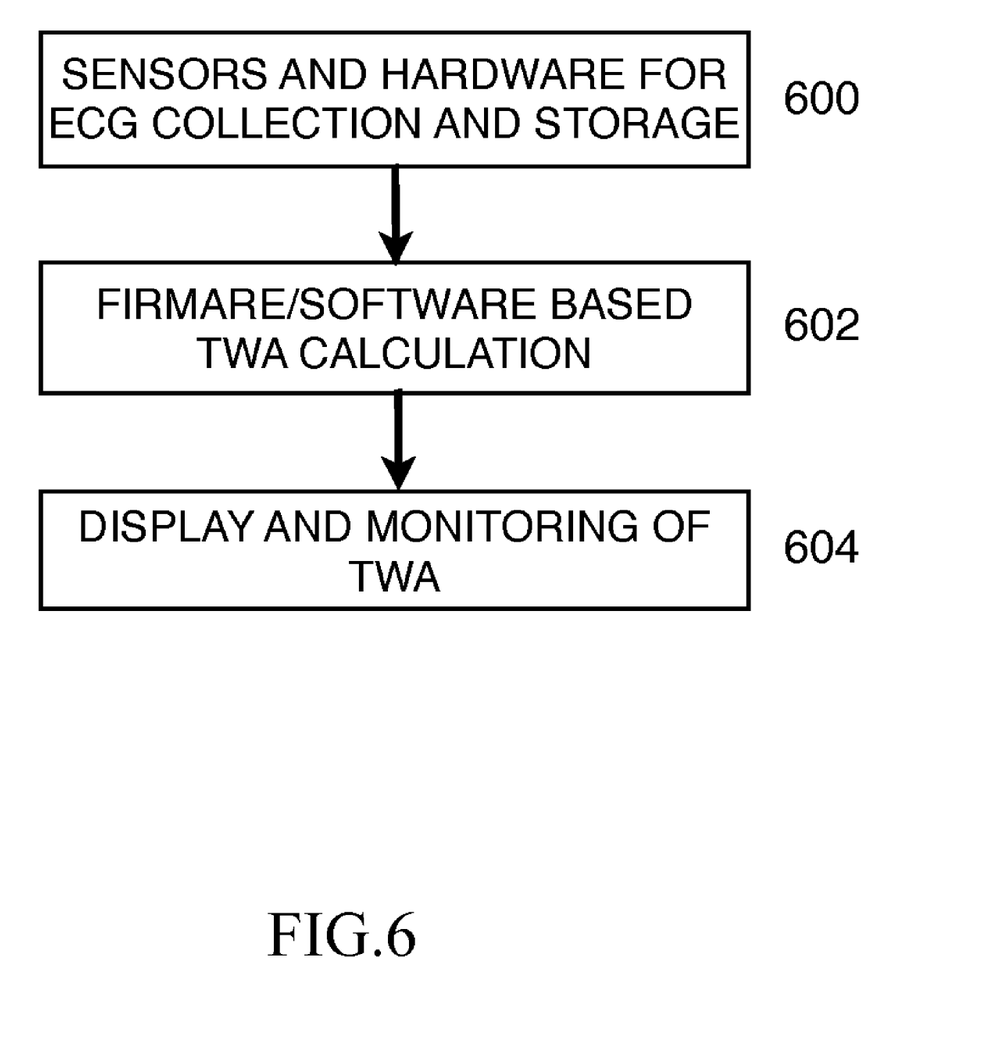
FIG. 6 shows a block diagram of an apparatus implementing the invention according to one embodiment.
Figure 7:
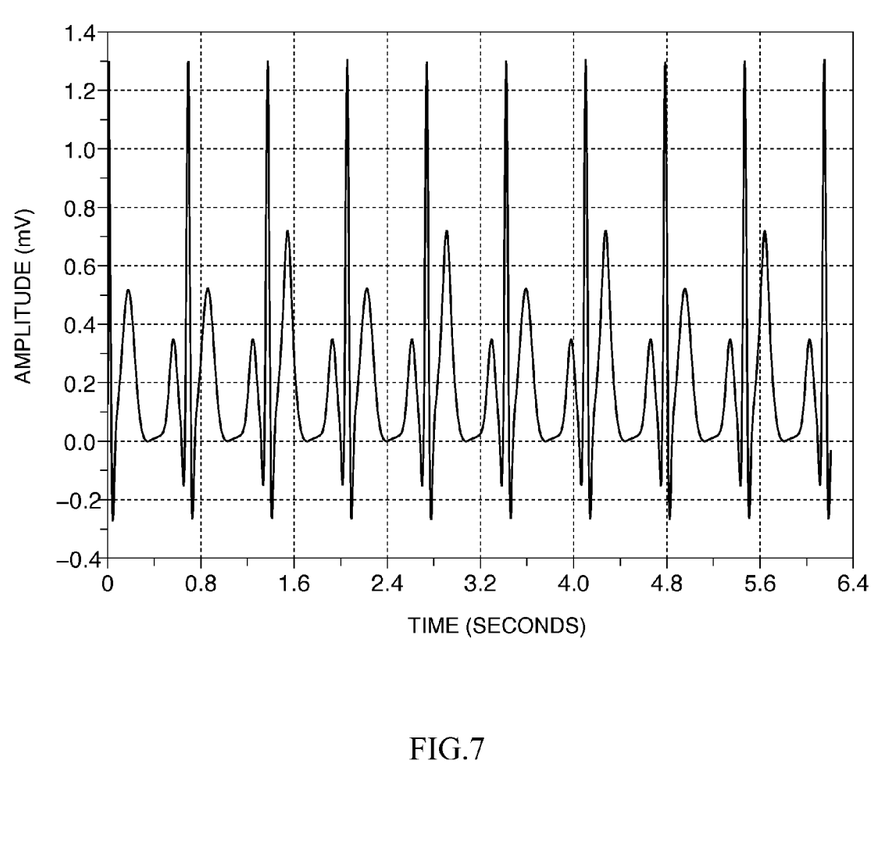
FIG. 7 shows an example electrocardiographic signal with T-wave alternans.

FIG. 1 shows a block diagram of the method for automatic analysis of TWA according to one embodiment; said method comprises the following method steps: (a) collecting and storing an ECG signal 100; (b) detecting each heartbeat T-wave in the ECG signal using an automatic detection and segmentation algorithm 102; (c) classifying said heartbeat T-wave as an even or odd heartbeat T-wave 104; (d) initializing said method by taking the first even and the first odd heartbeat T-wave as their respective initial average 106; (e) processing all the heartbeat T-waves in the ECG signal to generate an even heartbeat T-wave weighted average and odd heartbeat T-wave weighted average 108; and (f) calculating TWA using a distance metric between the even heartbeat weighted average and the odd heartbeat weighted average, said distance metric including curve matching 110. According to one embodiment said distance metric is computed as maximum absolute value of the difference between the event heartbeat. According to a second embodiment of the present invention, a method of curve matching is used prior to calculating the distance metric. In a third embodiment, the distance metric includes a similarity metric based on Dynamic Time Warping (DTW) 210. According to a forth embodiment, the distance metric is based on Continuous Dynamic Time Warping (CDTW) 310. The method can be implemented in firmware or software as part of a microcontroller or microprocessor-based apparatus for calculation of TWA. According to one embodiment, said apparatus FIG. 6 comprises: (a) sensors and data acquisition hardware to acquire and store said ECG signal 600; (b) means for processing said ECG signals using said method implemented in firmware or software in order to automatically calculate TWA 602; and (c) means for displaying said TWA including monitors, flat-panel displays, computer screens, PDAs, and smartphones 604.

Figure 4:
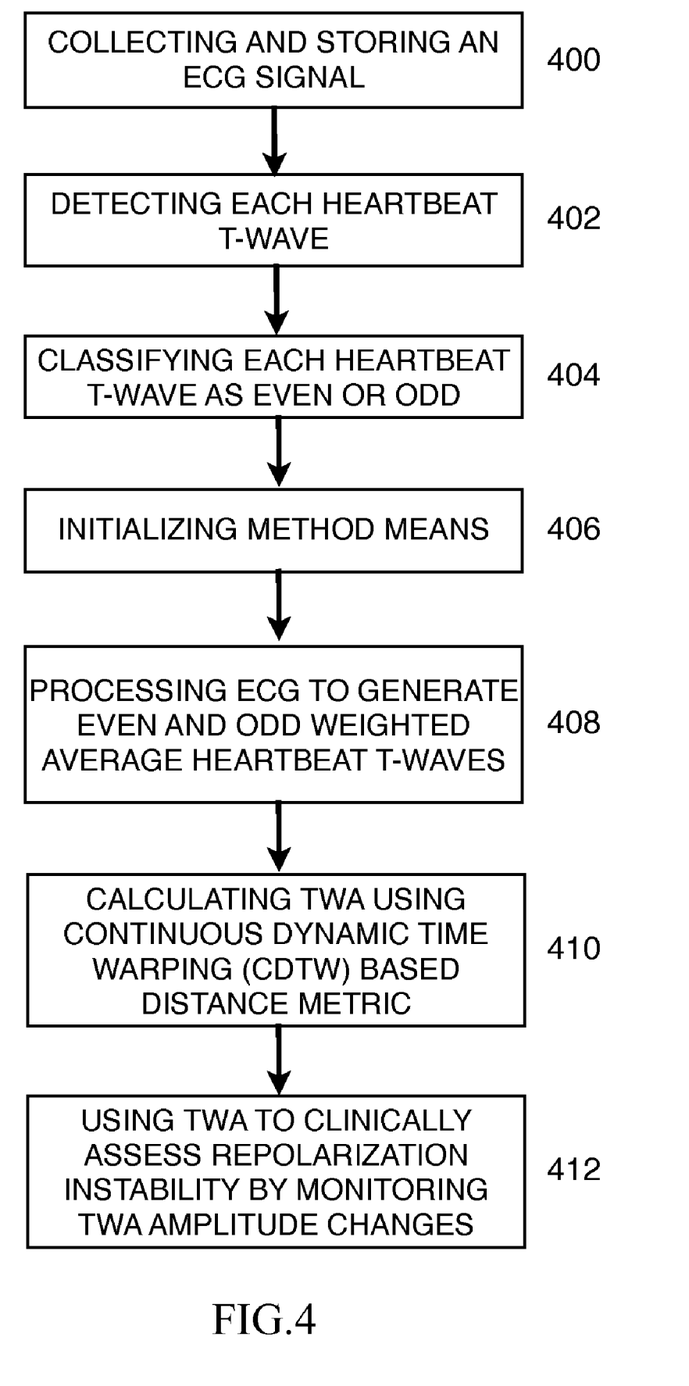
FIG. 4 shows a block diagram of an embodiment of the present invention to clinically assess repolarization instability.
Figure 5:
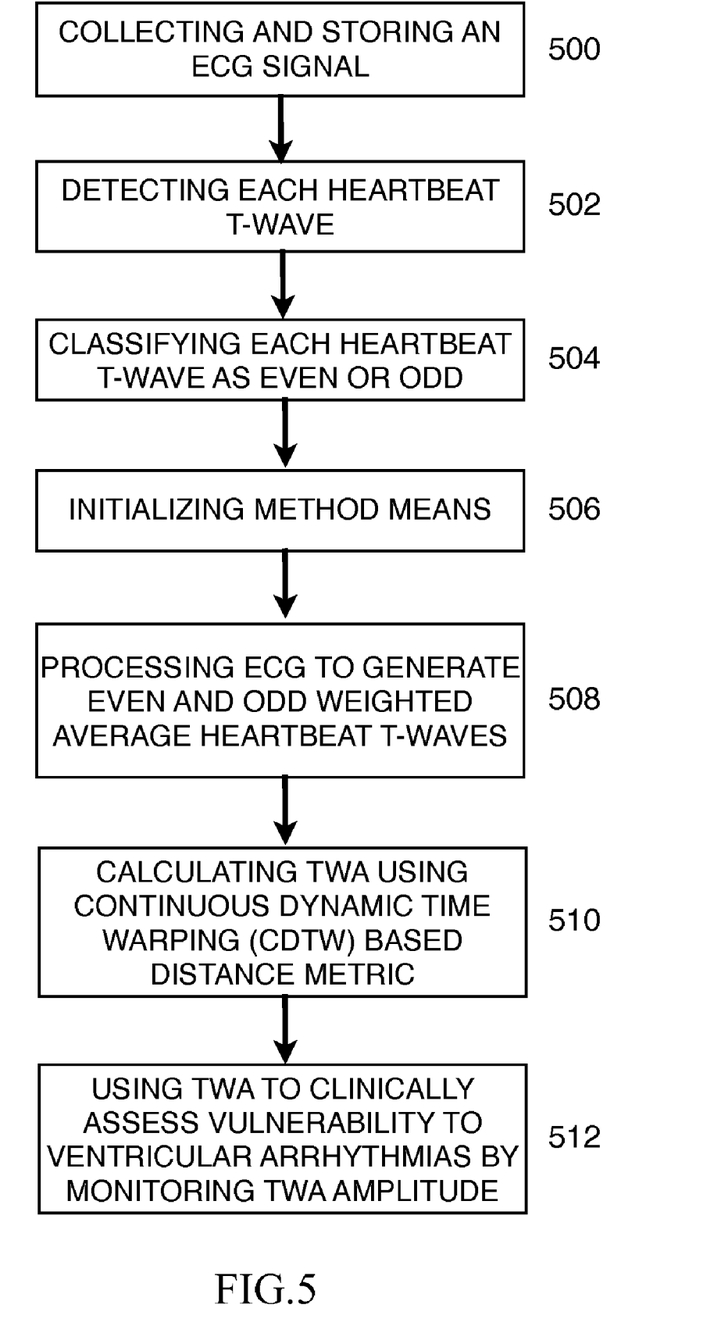
FIG. 5 shows a block diagram of an embodiment of the present invention to clinically assess ventricular arrhythmias.

The automatically calculated TWA can be used to conduct assessment of repolarization instability by analyzing the repolarization shape changes represented by TWA FIG. 4. Clinical findings support the diagnostic superiority of TWA versus QT interval analysis for several reasons. Abnormal T-waves frequently appear without significant QT interval changes. Changes in T-wave amplitude are different not only between patients with long QT syndrome and healthy subjects but also between patients with long QT syndrome with and without prior adverse cardiac events, despite having similar corrected QT interval durations. The calculated TWA metric can be used to clinically assess vulnerability to ventricular arrhythmias FIG. 5. TWA magnitude has been found to be linked to malignant arrhythmias under diverse clinical conditions: myocardial infarction and ischemia, heart failure, electrolyte disorders, cardiomyopathy, long QT syndrome, and drug intoxications [5]. Additionally, higher levels of TWA are correlated with a higher ventricular fibrillation risk.

According to one embodiment, the proposed method considers the electrocardiogram as a series of heartbeats (for TWA measurement purposes, only T waves or ST-T complexes are processed). Odd and even heartbeats are labeled as $A_n$ and $B_n$ respectively, where n as the order index. The ECG signal can then be defined as a combination sequence of consecutive $A_n$ and $B_n$ heartbeats:

$$ECG = \left\{ A_1, B_1, A_2, B_2, \ldots, A_{\frac{N}{2}}, B_{\frac{N}{2}} \right\}.$$

where N is the total number of heartbeats in the ECG, $A_n$ is the 2n−1 heartbeat, and $B_n$ is the 2n beat, for $$1 \leq n \leq \frac{N}{2}.$$

The length of each heartbeat is k. In general, k is different for each one, that is:

$$A_n = \{A_n(1), A_n(2), \ldots, A_n(k_{A_n})\},$$

and $$B_n = \{B_n(1), B_n(2), \ldots, B_n(k_{B_n})\}.$$

According to one embodiment a method for calculating TWA comprises the following method steps:

1. Initializing said method by taking the first heartbeat as the initial average:

$$\overline{A}_1 = A_1$$

2. Processing all the heartbeats in the series to update the weighted average accordingly $\overline{A}_n(i) = \overline{A}_{n-1}(i) + \Delta_i$, for $1 \leq n \leq N/2$, and $1 \leq i \leq k$. According to one embodiment, and without limitation, the updating factor $\Delta_i$ is calculated using the following rules:

$\Delta_i = -32$ if $\eta_i \leq -32$ $\Delta_i = \eta_i$ if $-1 \geq \eta_i \geq -32$ $\Delta_i = -1$ if $0 > \eta_i > -1$ $\Delta_i = 0$ if $\eta_i = 0$ $\Delta_i = 1$ if $1 \geq \eta_i > 0$ $\Delta_i = \eta_i$ if $32 \geq \eta_i > 1$ $\Delta_i = 32$ if $\eta_i \geq 32$ where $$\eta_i = \frac{1}{8}[A_n(i) - \overline{A}_{n-1}(i)].$$

Threshold values may vary depending on the heartbeat scale, and a temporal normalization is necessary in order to make $k_{A_n} = k_{A_{n-1}}$.

3. Obtaining a final average as the last computed weighted average, for $$n = \frac{N}{2}; \overline{A} = \overline{A}_{\frac{N}{2}}.$$

4. Repeating steps 1 to 3 for B series.
5. Calculating TWA as the maximum absolute value of the difference between $\overline{A}$ and $\overline{B}$, $d_{TWA} = \max|\overline{B} - \overline{A}|$.

According to another embodiment of the present invention, a method of curve matching is used prior to calculating the maximum absolute value of the difference $\overline{A}$ and $\overline{B}$, $d_{TWA} = \max|\overline{B} - \overline{A}|$. Curve matching methods have been widely applied in a variety of problems that yield data where the same phenomena exhibits variations at different positions or may have different durations. Analogously, the measurements for the single samples can have different time scales or axes, or the sample vectors may have different lengths. This applies to ECG heartbeats, and therefore, to TWA measurement. Dynamic Time Warping (DTW) is one of the numerous methods that have been proposed to correct time shifts. According to one embodiment of the present invention, DTW is used prior to calculating the distance metric in order to align the waveforms. DTW is described as a method that can eliminate shift-related artifacts from measurements by correcting a sample vector of length J towards a reference of length I. Identifying the global optimum for the warping path is transformed into an efficient iterative procedure divided into a forward step and a backward step:

Starting from point (1,1), and according to a minimization equation, constructing the mapping grid G(I,J), in which element G(i,j) is the optimal accumulated distance up to point (1,1) (forward step).

Determining the optimal warping path by backtracing from i(L), j(L)=(I,J) down to point (1,1) (backward step), where L is the alignment path length.

Synchronizing, usually L is larger than either I or J due to warping corrections. The extent of elongation is unpredictable until the warping process is finished and may vary from sample to sample. An additional synchronization step yielding vectors of length I is required [17].

According to one embodiment of the present invention, DTW is applied to the waves prior to said distance calculation. In order to apply DTW to the alignment of a pair of heartbeats, ST-T complexes, or T waves $A_n$ and $A_m$, these waves are represented in a 2-D space: $A_n\{P_n(t), t=1, \ldots, k_{A_n}\}$, and $A_m = \{P_m(t), t=1, \ldots, k_{A_m}\}$. This embodiment assumes there is a correspondence map between these two curves, $\phi = [\phi A_n(t), \phi A_m(t)] | P_n(\phi A_n(t)) \in A_n$ corresponds to a point $P_m(\phi A_m(t)) \in A_m$, $t \in \{1, \ldots, L\}$. The dissimilarity $S_d$ between these two curves is computed as:

$$S_d(A_n, A_m) = \sum_{t=2}^{T} d((A_{n(\varphi A_n(t-1))}, A_{m(\varphi A_m(t-1))}),$$ (1)

$$(A_{n(\varphi A_n(t))}, A_{m(\varphi A_m(t))}))$$

$$= \sum_{t=2}^{T} \left\| \overrightarrow{A_{n(\varphi A_n(t))} A_{m(\varphi A_m(t))}} - \overrightarrow{A_{n(\varphi A_n(t-1))} A_{m(\varphi A_m(t-1))}} \right\|^2$$

where $\|\cdot\|^2$ denotes the Euclidean norm.

The objective of curve matching in this embodiment is to find the alignment path between $A_n$ and $A_m$ that minimizes the dissimilarity. Analytically, this objetive is defined as:

$$\varphi = [\varphi_{A_n}, \varphi_{A_m}]^T = \operatorname*{argmin}_{\varphi}\{S_d(A_n, A_m)\}$$ (2)

According to one embodiment, and without limitation, the solution to this minimization problem can be achieved by means of dynamic programming as follows:

$$S_d(\varphi(t)) = \min_{\varphi(t-1)} \{S_d(\varphi(t-1)) +$$ (3)

$$d((A_{n(\varphi A_n(t-1))}, A_{m(\varphi A_m(t-1))}), (A_{n(\varphi A_n(t))}, A_{m(\varphi A_m(t))}))\}$$

where $d((A_n(\phi A_{n(t-1)}), A_{m(\phi A_{m(t-1)})}), (A_{n(\phi A_{n(t)})}, A_{m(\phi A_{m(t)})}))$ accounts for the distance between a pair of aligned samples of $A_n$ and $A_m$. Graphically, this procedure corresponds to finding the optimal warping path on the mapping grid G(I,J). In principle, the path can reach any node in the grid. However, constrained DTW is superior to unconstrained DTW since the last is too flexible, resulting in an overfitting of the observed shifts in some cases.

According to another embodiment, continuous DTW (CDTW) is employed instead of the standard DTW. Standard discrete DTW suffers from some drawbacks, most importantly the fact that it is defined between sequences of points rather than curves. The way in which a curve is sampled to yield such sequence can dramatically affect the quality of the alignment [10]. For example, the result of discrete alignment exhibits edges that might introduce measurement errors. In contrast, a continuous version of DTW (CDTW) does not suffer from this drawback, since a point in $A_n$ is allowed to match a point between two samples in $A_m$. In CDTW the recursion equation is the same as Eq.3, with the additional condition that if $\phi_{A_n}(t)$ takes values on $\{1, \ldots, k_{A_n}\}$, then $\phi_{A_m}(t)$ is allowed to take non-integer values, and viceversa. According to one embodiment, this is accomplished by means of a linear interpolation model assumed for the curves, that is, new intermediate matching points are computed by a curve parameterization method:

$$A_n = \begin{cases} x = x(i-1) + r\frac{\Delta_x}{\Delta} \\ y = y(i-1) + r\frac{\Delta_y}{\Delta} \end{cases}$$

where x(i−1) and y(i−1) represent the coordinates of a point of the wave, and x and y represent a calculated new point. r is the independent variable. The parameters are defined as follows:

$$\Delta_x = (i) - x(i-1)$$

$$\Delta_y = y(i) - y(i-1)$$

$$\Delta = \sqrt{\Delta_x^2 + \Delta_y^2}$$

For a unidimensional curve, $\Delta_x$ becomes 1, and $\Delta_y = A_n(i) - A_n(i-1)$. The same applies to $A_m$.

DTW equations are updated accordingly to fit in CDTW. The output of the method is an optimal alignment between input waves $A_n$ and $A_m$. Thus, according to one embodiment, the proposed method (EMMA) described here adds a CDTW-based alignment to the standard MMA method. The method steps are the same as in MMA, but in the last one, the dissimilarity between the two averages is computed using CDTW instead: $d_{TWA}=\max|\overline{B}-\overline{A}|_{CDTW}$, that is, $\overline{B}$ and $\overline{A}$ are aligned as described prior to finding the maximum difference between them.

While particular embodiments of the present invention have been described, it is understood that modifications and generalizations will be apparent to those skilled in the art without departing from the spirit of the invention.

Operation and Testing of Proposed Emma Method

The following is a description of an actual reduction to practice of one embodiment (EMMA, based on CDTW curve matching) of the invention and the results of an assessment study designed to test and compare its performance against MMA (distance metric without alignment). Unfortunately, there is no gold standard public TWA database annotated by experts [8] as in other similar fields [3]. In order to provide an objective assessment of TWA analysis methods, it is important to know parameters in advance (waveform location, amplitude, beginning, end, noise and artifacts, etc) which currently can only be achieved by designing a simulation study with synthetic ECGS. Some researchers have created ECG registers by replication of a real or synthetic single noiseless heartbeat to which different kinds of noise and alternans episodes were added [4, 7], but the resulting signals do not include the physiological variability that may influence TWA analysis. Others have included real recorded physiological noise and time scaled basic heartbeat to better simulate a real ECG [8]. In a few studies, researchers have used real noiseless annotated ECG signals, added real physiological noise, and only TWA were synthetic. These signals achieved very realistic registers although not all the parameters were known. A few clinical studies have used real ECGs with real TWA. However, these datasets are not publicly available, do not have a goldstandard for algorithm assessment, and often are very specific to a certain cardiac disorder or experimental set or were obtained invasively.

Our assessment study uses synthetic ECG registers with known parameters. In order to achieve a high degree of realism, we used the synthetic ECG generator recently developed and described in [9]. This method enabled us to determine the positions and limits of the different waves, change the heart rate, use variable levels of TWA and noise, and add baseline wander.

In the synthetic ECG generator, users can specify ECG parameters of the ECG such the mean and standard deviation of the heart rate, morphology of the PQRST cycle, amplitude, sampling frequency, and the power spectrum of the RR tachogram. The model generates a trajectory in a 3D state space with coordinates (x,y,z) where semiperiodicity of the ECG corresponds to the rotation of the trajectory in an attracting limit cycle of unit radius in the (x,y) plane. Each revolution on this circle corresponds to one heartbeat. Interbeat variation in the ECG is simulated using the motion of the trajectory in the z direction. Different points on the ECG, such as P, Q, R, S and T waves, are described by events corresponding to negative and positive attractors/repellors in the z direction. These events are placed at fixed angles along the unit circle given by $\theta_P$, $\theta_Q$, $\theta_R$, $\theta_S$, $\theta_T$. All these values were experimentally set by real ECG analysis [9]. Synthetic TWA was created by adding a Hamming function to the T wave every two beats.

Experiments were conducted for several cases in order to assess TWA measurement accuracy using the MMA benchmark and one embodiment of the proposed invention, the EMMA method (e.g. embodiment using Continuous Dynamic Time Warping for curve matching). The parameters used to generate the test data were taken from similar works [15]:

Levels of TWA: 10, 20, 50, 100, 200, 500, and 1000 µV.

16 heartbeats epochs. Choice of an appropriate time window for TWA analysis is not straightforward. Selection of a long window might hinder detection of short transients, whereas selection of a short window would increase the influence of spurious artifacts on the results. Final TWA measurement corresponds to the average of measurements obtained for each epoch in the ECG register.

Heart rate increasing from 60 to 120 bpm, in 10 bpm increments where the length of cardiac complexes was scaled according to the change in heart rate. Results were averaged in order to reduce the amount of data.

Phase reversals (5 phase shifts/min).

Different levels σ of random noise to assess the accuracy and robustness of each method: 5, 10, 25, 50, 100, 200, and 300 µV.

Simulated baseline wandering (changing amplitude and frequency).

Input signals underwent no preprocessing or treatment aimed at improving signal quality; TWA was measured directly. Results shown correspond to those obtained by averaging partial results for all the heartbeat rates.

First, robustness against noise for several TWA levels was analyzed. Results shown in Table 1 correspond to TWA ranging from 0 to 20 µV for all the noise levels mentioned above. Table 2 shows results for TWA level from 50 to 1000 µV.

TABLE 1

TWA amplitude measurements using standard MMA and EMMA methods, for real amplitudes ranging from 0 µV to 20 µV.

| Noise σ | TWA = 0 µV | | TWA = 2 µV | | TWA = 5 µV | | TWA = 10 µV | | TWA = 20 µV | |
|---|---|---|---|---|---|---|---|---|---|---|
| | MMA | EMMA | MMA | EMMA | MMA | EMMA | MMA | EMMA | MMA | EMMA |
| 0 µV | 3.0 | 2.6 | 4.1 | 3.8 | 6.2 | 5.7 | 10.2 | 10.0 | 20.1 | 20.0 |
| 5 µV | 14.0 | 11.0 | 14.2 | 11.0 | 15.5 | 11.5 | 18.6 | 13.8 | 27.2 | 22.3 |
| 10 µV | 26.1 | 20.1 | 26.3 | 20.2 | 27.3 | 20.5 | 29.7 | 21.5 | 36.6 | 27.1 |
| 25 µV | 63.7 | 51.0 | 63.8 | 51.1 | 64.4 | 51.3 | 66.0 | 51.6 | 71.0 | 46.0 |
| 50 µV | 126.2 | 103.5 | 126.3 | 103.6 | 126.6 | 103.9 | 127.6 | 104.0 | 130.8 | 104.8 |
| 100 µV | 251.8 | 217.4 | 252.0 | 217.5 | 252.2 | 217.7 | 252.8 | 218.0 | 254.8 | 218.3 |
| 200 µV | 503.3 | 472.8 | 503.5 | 472.9 | 503.8 | 472.9 | 504.3 | 473.1 | 505.7 | 472.7 |
| 300 µV | 798.5 | 779.3 | 798.7 | 779.7 | 799.1 | 779.9 | 799.5 | 779.5 | 801.0 | 779.8 |

TABLE 2

TWA amplitude measurements using standard MMA and EMMA methods, for real amplitudes ranging from 50 μV to 1000 μV.

| Noise σ | TWA = 50 μV | | TWA = 100 μV | | TWA = 200 μV | | TWA = 500 μV | | TWA = 1000 μV | |
|---|---|---|---|---|---|---|---|---|---|---|
| | MMA | EMMA | MMA | EMMA | MMA | EMMA | MMA | EMMA | MMA | EMMA |
| 0 μV | 50.0 | 50.0 | 100.0 | 100.0 | 200.0 | 200.0 | 500.0 | 500.0 | 1000.0 | 1000.0 |
| 5 μV | 56.4 | 52.1 | 105.8 | 102.0 | 205.1 | 201.8 | 503.9 | 501.1 | 1002.6 | 1000.2 |
| 10 μV | 63.9 | 54.5 | 112.8 | 104.3 | 211.6 | 203.9 | 509.2 | 502.9 | 1006.8 | 1001.3 |
| 25 μV | 91.6 | 69.1 | 135.9 | 112.6 | 233.0 | 211.3 | 527.7 | 509.4 | 1022.0 | 1006.5 |
| 50 μV | 146.4 | 111.5 | 181.6 | 138.4 | 270.0 | 223.9 | 560.2 | 519.7 | 1049.6 | 1015.2 |
| 100 μV | 266.6 | 221.5 | 292.3 | 232.5 | 362.0 | 284.3 | 631.7 | 542.8 | 1112.6 | 1034.7 |
| 200 μV | 512.6 | 474.2 | 531.1 | 477.3 | 583.6 | 496.4 | 800.1 | 651.4 | 1266.1 | 1106.9 |
| 300 μV | 807.5 | 783.0 | 823.6 | 788.1 | 868.0 | 809.0 | 1037.6 | 908.8 | 1360.7 | 1146.3 |

Since common noise levels found in TWA analysis range mainly between 10 and 20 μV in these cases, specific experiments were carried out using more noise levels in this interval, as shown in Table 3.

TABLE 3

TWA amplitude measurements using standard MMA and EMMA methods for noise levels of 15 and 20 μV.

| Noise σ | TWA = 0 μV | | TWA = 5 μV | | TWA = 20 μV | | TWA = 100 μV | | TWA = 500 μV | |
|---|---|---|---|---|---|---|---|---|---|---|
| | MMA | EMMA | MMA | EMMA | MMA | EMMA | MMA | EMMA | MMA | EMMA |
| 15 μV | 37.9 | 26.7 | 38.9 | 26.9 | 47.5 | 29.5 | 120.5 | 100.2 | 515.5 | 498.4 |
| 20 μV | 50.5 | 35.8 | 51.3 | 36.0 | 58.9 | 37.6 | 128.1 | 100.4 | 521.5 | 498.2 |

In TWA analysis, there are other artifacts that may influence measurement, such as baseline wandering. Some experiments were conducted to assess the comparative performance of MMA and EMMA methods under two baseline wandering conditions termed $L_1$ and $L_2$. Both were created using a sinusoid of frequency 0.25 Hz, and amplitude 0.5 mV and 0.05 mV respectively. A noise level of 5 μV was also added. Results for this case are shown in Tables 4 and 5.

Phase shifts may also occur in registers with TWA. Sometimes a phase reversal is triggered so that alternans pattern changes, that is, heartbeat series become . . . ABABBABABA . . . or . . . ABABAABAB . . . An uncorrected phase reversal can mistakenly modify the TWA estimate [13]. MMA method is intrinsically robust to these phase shifts, and

TABLE 4

TWA amplitude measurements using standard MMA and EMMA methods, for two baseline wandering and noise scenarios. All values in μV.

| Baseline | TWA = 0, σ = 0 | | TWA = 0, σ = 5 | | TWA = 2, σ = 0 | | TWA = 2, σ = 5 | | TWA = 5, σ = 0 | |
|---|---|---|---|---|---|---|---|---|---|---|
| | MMA | EMMA | MMA | EMMA | MMA | EMMA | MMA | EMMA | MMA | EMMA |
| $L_1$ | 18.8 | 12.3 | 10.8 | 8.5 | 19.ic9 | 12.3 | 11.1 | 8.8 | 19.4 | 13.1 |
| $L_2$ | 16.4 | 11.1 | 8.1 | 7.7 | 16.4 | 11.1 | 8.1 | 7.8 | 16.8 | 11.5 | these experimental set was aimed at assessing the vulnerability of EMMA to it in comparison to MMA method.

TABLE 5

TWA amplitude measurements using standard MMA and EMMA methods, for two baseline wandering and noise scenarios. All values in μV.

| Baseline | TWA = 5, σ = 5 | | TWA = 10, σ = 0 | | TWA = 10, σ = 5 | | TWA = 20, σ = 0 | | TWA = 20, σ = 5 | |
|---|---|---|---|---|---|---|---|---|---|---|
| | MMA | EMMA | MMA | EMMA | MMA | EMMA | MMA | EMMA | MMA | EMMA |
| $L_1$ | 10.8 | 8.5 | 13.8 | 12.1 | 21.6 | 15.5 | 20.2 | 20.0 | 26.9 | 21.9 |
| $L_2$ | 8.0 | 7.7 | 11.1 | 10.1 | 19.2 | 13.4 | 20.2 | 20.0 | 26.9 | 21.9 |

Tables 6 and 7 show the results obtained in this case. Several noise levels were also added.

TABLE 6

TWA amplitude measurements using standard MMA and EMMA methods, for phase shifts. All values in μV.

|  | TWA = 10, σ = 0 | | TWA = 10, σ = 5 | | TWA = 20, σ = 0 | | TWA = 20, σ = 5 | | TWA = 20, σ = 10 | |
| --- | --- | --- | --- | --- | --- | --- | --- | --- | --- | --- |
|  | MMA | EMMA | MMA | EMMA | MMA | EMMA | MMA | EMMA | MMA | EMMA |
| Phase shift | 10.4 | 9.9 | 18.8 | 13.2 | 19.8 | 19.6 | 27.3 | 22.5 | 37.1 | 27.1 |

TABLE 7

TWA amplitude measurements using standard MMA and EMMA methods, for phase shifts. All values in μV.

|  | TWA = 50, σ = 0 | | TWA = 50, σ = 5 | | TWA = 50, σ = 10 | | TWA = 50, σ = 25 | |
| --- | --- | --- | --- | --- | --- | --- | --- | --- |
|  | MMA | EMMA | MMA | EMMA | MMA | EMMA | MMA | EMMA |
| Phase shift | 49.9 | 49.8 | 55.8 | 51.5 | 62.7 | 53.5 | 92.1 | 69.6 |

Another important source of errors in TWA measurement is ECG fiducial point detection accuracy (QRS or T detection, mainly). Incorrect detection of T wave apex may introduce a bias in the computation of the TWA. In order to assess the performance of EMMA versus MMA method in this case, additional experiments were conducted with random shifts of T waves peak position (±15 ms). Results are shown in Table 8.

Experiments assessed the performance of MMA and EMMA methods under different conditions of noise level, heart rate, and TWA amplitude. Results were obtained in an unfavourable scenario of no signal preprocessing to reduce noise or any other artifacts such as baseline wandering. The objective was to conduct a comparative analysis between EMMA and MMA under the same conditions.

For TWA=0 μV, that is, registers without TWA, both methods yielded measures greater than 0, even for σ=0 μV. This is because synthetic registers have a small, but not negligible, wave amplitude variation. As the noise level increases up to 300 μV, TWA measurement error increases too. EMMA method yields TWA=2*σ, whereas MMA method yields TWA=2.5*7, namely, MMA error is 25% greater in most cases. The same occurs for TWA=2 μV. It does not mean MMA and EMMA methods can not detect TWA levels below 2 μV, since registers between EMMA and MMA methods, not at obtaining absolute measures.

Figure 8:
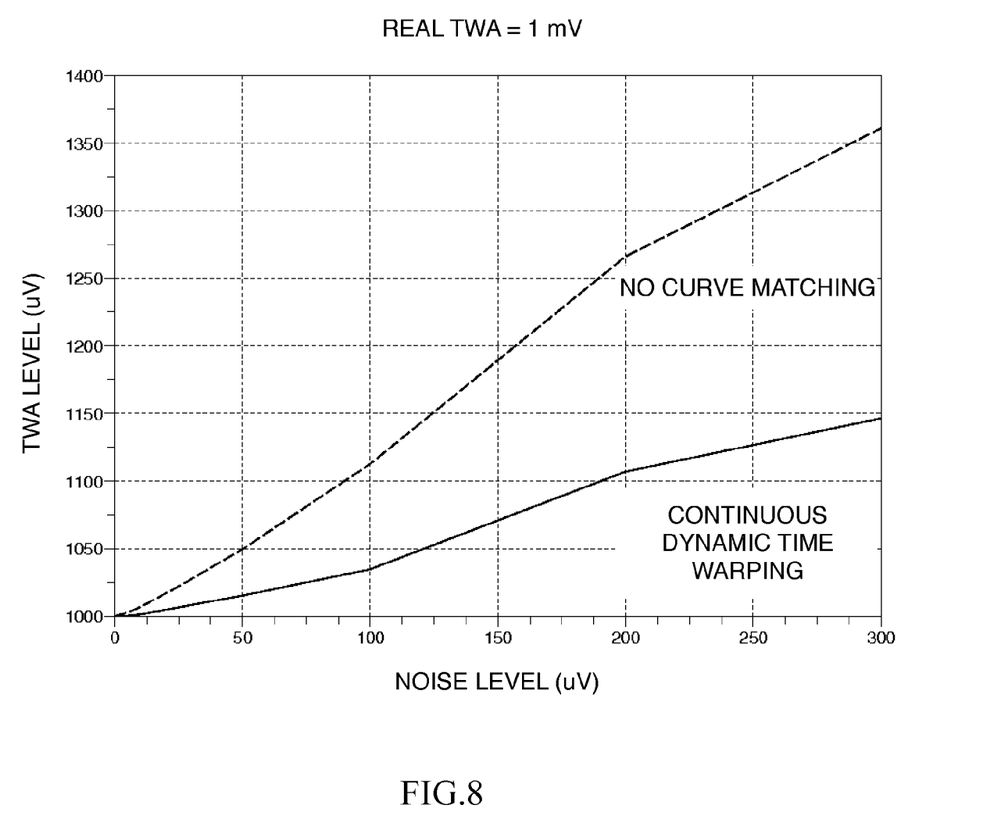
FIG. 8 shows the results of an assessment study comparing the accuracy of TWA calculation directly using a distance metric versus using Continuous Dynamic Time Warping.

At TWA=5 μV, MMA and EMMA methods yield acceptable results for non-noisey registers, but for the rest of the cases, MMA error is again 25% greater, up to very distorted signals (200 μV noise level and above). This demonstrates that the EMMA method is more robust against noise. This is confirmed in the rest of the TWA levels. The EMMA method yields acceptable results for a noise level above that of MMA as can be observed in FIG. 8. The MMA and EMMA methods perform equally well for very high SNR signals (noise amplitude tends to 0), but EMMA is more robust to noise and enables us to get correct TWA measures under worse noise conditions than standard MMA. This is because curve matching also aligns noise peaks and therefore the TWA measure is less influenced by noise amplitude.

The experiments under different baseline wandering conditions also demonstrated that EMMA is more robust than MMA in these circumstances (Table 4). The effect of baseline wandering is an increase in the low detection threshold for TWA amplitude because of the additional wave amplitude offset. Results start to be significant from TWA 101V. For $L_1$

TABLE 8

TWA amplitude measurements using standard MMA and EMMA methods, with T wave position errors.

|  | TWA = 0 μV | | TWA = 5 μV | | TWA = 20 μV | | TWA = 100 μV | | TWA = 500 μV | |
| --- | --- | --- | --- | --- | --- | --- | --- | --- | --- | --- |
| Noise σ | MMA | EMMA | MMA | EMMA | MMA | EMMA | MMA | EMMA | MMA | EMMA |
| 0 μV | 80.5 | 69.3 | 84.3 | 72.6 | 80.1 | 68.6 | 119.9 | 112.7 | 504.3 | 499.9 |
| 5 μV | 86.3 | 71.3 | 84.9 | 70.0 | 86.0 | 70.6 | 124.5 | 112.1 | 508.5 | 499.2 |
| 50 μV | 168.7 | 124.4 | 173.2 | 127.2 | 167.2 | 123.8 | 196.7 | 136.0 | 562.3 | 494.9 | where not preprocessed. Actually, in a real case, it is very unlikely to have noise levels greater than TWA levels, but experiments were aimed at assessing comparative accuracy (0.5 mV amplitude) and low TWA, MMA result is about 40% higher than EMMA's. For TWA levels of 10 μV and 20 μV results are equal when no noise is present, but MMA result is again 25% higher for $\sigma=5$ μV. This is due to the alignment effect of EMMA, it tends to compensate wave differences as it also matches the baselines.

When there are phase shifts in the register, EMMA is again more accurate and robust. When no noise is present, results are equal (slightly better for EMMA if TWA=10μ, and better for MMA in the rest). With some noise, EMMA outperforms MMA in all cases by 25%. Since EMMA is based on MMA, the effect on the results of the phase shifts is negligible if noise is present, namely, there are no differences between EMMA and MMA as for phase shifts provided there is no noise in the signals. However, this is an unrealistic case because even after signal filtering, it is almost impossible to remove all the noise in a real signal.

Wave detection errors also add measurement bias since peaks are not correctly aligned. In all cases tested, EMMA results were more accurate, although measurements started to be acceptable for TWA greater than 100 μV. However, it has to be noted that heart rate is important in this case since 15 ms fiducial point shift is more significant for 120 bpm than for 60 bpm.

We described an embodiment of the proposed method to improve the accuracy of the MMA TWA analysis, based on CDTW curve alignment. The results of our assessment study demonstrate EMMA to be more accurate than MMA. Specifically, our proposed method is more robust against noise, baseline wandering, phase shifts, and wave detection errors. In general, EMMA results were 25% more accurate than MMA's.

The EMMA embodiment is simple to implement and computationally inexpensive. In another embodiment of the present invention, accuracy can be further improved since curve alignment was only applied at the last stage of the distance calculation between averages $\overline{A}$ and $\overline{B}$, namely, intermediate averaging was computed without wave alignment, just wave length normalization. Thus, some alignment errors are already present before final curve matching takes place.

While particular embodiments of the present invention have been described, it is understood that modifications and generalizations will be apparent to those skilled in the art without departing from the spirit of the invention.

REFERENCES

[1] Burak Acar. New approaches to t-wave analysis from surface ecg. *Cardiac Electrophysiology Review*, 3(4):319-323, 1999.
[2] L. Burattini, W. Zareba, J. P Couderc, E. L Titlebaum, and A. J. Moss. Computer detection of non-stationary t wave alternans using a new correlation method. In *Proceedings of Computers in Cardiology*, volume 24, pages 657-660, 1997.
[3] A. L. Goldberger, L. A. N. Amaral, L. Glass, J. M. Hausdorff, P. Ch. Ivanov, R. G. Mark, J. E. Mietus, G. B. Moody, C.-K. Peng, and H. E. Stanley. Physiobank, physiotoolkit, and physionet: Components of a new research resource for complex physiologic signals. *Circulation*, 101(23):e215-e220, 2000. Circulation Electronic Pages: http://circ.ahajournals.org/cgi/content/full/101/23/e215.
[4] D. Janusek, M. Kania, and R. Maniewski. Effect of electrocardiogram signal quality on t-wave alternans measurements: A simulation study. Number 33, pages 505-508, 2006.
[5] Elizabeth S. Kaufman, Judith A. Mackall, Birendra julka, Carole Drabek, and David S. Rosenbaum. Influence of heart rate and sympathetic stimulation on arrhythmogenic t wave alternans. *American Journal of Physiology—Heart and Circulation Physiology*, (279):1248-1255, 2000.
[6] Marek Malik. Assessment of t-wave morphology. In *Mayo Clintc Proceedings*, volume 78, pages 18-20, January 2003.
[7] J. P Martinez, S. Olmos, and P. Laguna. T wave alternans detection: A simulation study and analysis of european st-t database. (27):155-158, 2000.
[8] Juan P. Martinez and Salvador Olmos. Methodological principles of t wave alternans analysis: A unified framework. *IEEE Transactions on Biomedical Engineering*, pages 599-613, April 2005.
[9] Patrick E. McSharry, Gari D. Clifford, Lionel Tarassenko, and Leonard A. Smith. A dynamical model for generating synthetic electrocardiogram signals. *IEEE Transactions on Biomedical Engineering*, 50(3):289-294, March 2003.
[10] Mario E. Munich and Prieto Perona. Continuous dynamic time warping for translationinvariant curve alignment with applications to signature verification. In *Proceedings of 7th International Conference on Computer Vision*, 1999.
[11] S Narayan. T-wave alternans and the susceptibility to ventricular arrhythmias. *J. Am. Coll. Cardiology*, pages 269-281, December 2006.
[12] B. D. Nearing, A. H. Huang, and Verrier R. L. Dynamic tracking of cardiac vulnerability by complex demodulation of the t wave. *Science*, 252(5004):437-440, 1991.
[13] Bruce D. Nearing and Richard L. Verrier. Modified moving average analysis of t-wave alternans to predict ventricular fibrillation with high accuracy. *Journal of Applied Physiology*, 92:541-549, February 2002.
[14] Y. Serinagaoglu, D. Sabuncuoglu, and Y. Z Ider. Spectral analysis of t wave alternans signal. In *Proceeding of 18th Annual International Conference of the IEEE Engineering in Medicine and Biology Society*, pages 1353-1354, 1996.
[15] Vladimir Shusterman and Anna Goldberg. Tracking repolarization dynamics in real-life data. *Journal of Electrocardtology*, 37:180-186, 2004.
[16] Pawell Strumillo and Jan Ruta. Poincare mapping for detecting abnormal dynamics of cardiac repolarization. *IEEE Engineering in Medicine and Biology*, pages 62-65, January 2002.
[17] G Tomasi, F van den Berg, and C Anderson. Correlation optimized warping and dynamic time warping as preprocessing methods for chromatographic data. *Journal of Chemometric*, pages 231-241, July 2004.
[18] Richard L. Verrier, Kevin F. Kwaku, Bruce D. Nearing, and Mark E. Josephson. T-wave alternans: Does size matter? *Journal of Cardiovascular Electrophysiology*, 16(6):625-628, June 2005.

The invention claimed is:
1. A method for automatic analysis of T-wave alternans (TWA) comprising the following method steps:
(a) collecting and storing an electrocardiogram (ECG) signal;
(b) detecting each heartbeat T-wave in the ECG signal using an automatic detection and segmentation algorithm;
(c) classifying said heartbeat T-wave as an even or odd heartbeat T-wave;
(d) initializing said method by taking the first even and the first odd heartbeat T-wave as their respective initial average;
(e) processing all the heartbeat T-waves in the ECG signal to generate an even heartbeat T-wave weighted average and odd heartbeat T-wave weighted average; and

(f) calculating TWA using a distance metric requiring alignment between the even heartbeat weighted average and the odd heartbeat weighted average, said distance metric includes a curve matching algorithm employing Continuous Dynamic Time Warping (CDTW) in order to optimally align said even heartbeat weighted average and the odd heartbeat weighted average.

2. A method for assessment of repolarization instability and assessment of vulnerability to ventricular arrhythmias, said method comprising:
  (a) collecting and storing an electrocardiogram (ECG) signal;
  (b) detecting each heartbeat T-wave in the ECG signal using an automatic detection and segmentation algorithm;
  (c) classifying said heartbeat T-wave as an even or odd heartbeat T-wave;
  (d) initializing said method by taking the first even and the first odd heartbeat T-wave as their respective initial average;
  (e) processing all the heartbeat T-waves in the ECG signal to generate an even heartbeat T-wave weighted average and odd heartbeat T-wave weighted average;
  (f) calculating a T-wave alternans metric (TWA) using a curve-matching based distance metric between the even heartbeat weighted average and the odd heartbeat weighted average employing Continuous Dynamic Time Warping (CDTW); and
  (g) using said TWA to clinically assess repolarization instability and assess vulnerability to ventricular arrhythmias by monitoring TWA amplitude changes.

3. An apparatus for automatic determination of T-wave alternans from an electrocardiographic signal (ECG), comprising:
  (a) a processor configured for 1) collecting and storing an ECG signal, 2) detecting each heartbeat T-wave in the ECG signal using an automatic detection and segmentation algorithm, 3) classifying said heartbeat T-wave as an even or odd heartbeat T-wave, 4) initializing said method by taking the first even and the first odd heartbeat T-wave as their respective initial average, 5) processing all the heartbeat T-waves in the ECG signal to generate an even heartbeat T-wave weighted average and odd heartbeat T-wave weighted average, and 6) calculating TWA using a distance metric requiring alignment between the even heartbeat weighted average and the odd heartbeat weighted average, said distance metric includes a curve matching algorithm employing Continuous Dynamic Time Warping (CDTW) in order to optimally align said even heartbeat weighted average and the odd heartbeat weighted average; and
  (b) outputting said TWA.

* * * * *